US009915624B2

(12) United States Patent
Turovets et al.

(10) Patent No.: US 9,915,624 B2
(45) Date of Patent: Mar. 13, 2018

(54) OPTICAL METROLOGY FOR IN-SITU MEASUREMENTS

(71) Applicant: NOVA MEASURING INSTRUMENTS LTD., Rehovot (IL)

(72) Inventors: Igor Turovets, Moshav Givat Yarim (IL); Cornel Bozdog, Boise, ID (US); Dario Elyasi, Jerusalem (IL)

(73) Assignee: NOVA MEASURING INSTRUMENTS, LTD., Rehovot (IL)

( * ) Notice: Subject to any disclaimer, the term of this patent is extended or adjusted under 35 U.S.C. 154(b) by 0 days.

(21) Appl. No.: 15/385,495

(22) Filed: Dec. 20, 2016

(65) Prior Publication Data

US 2017/0167987 A1 Jun. 15, 2017

Related U.S. Application Data

(63) Continuation of application No. 14/422,190, filed as application No. PCT/IL2013/050697 on Aug. 15, 2013, now Pat. No. 9,528,946.

(Continued)

(51) Int. Cl.
*G01N 21/00* (2006.01)
*G01N 21/95* (2006.01)
(Continued)

(52) U.S. Cl.
CPC ......... *G01N 21/9501* (2013.01); *G01B 11/06* (2013.01); *G01B 11/24* (2013.01); *G01N 21/47* (2013.01); *G01B 2210/56* (2013.01)

(58) Field of Classification Search
CPC .... G01B 11/24; G01B 11/06; G01B 2210/56; G01N 21/9501; G01N 21/47
See application file for complete search history.

(56) References Cited

U.S. PATENT DOCUMENTS

| 6,764,379 B2 | 7/2004 | Finarov |
| 2001/0003084 A1 | 6/2001 | Finarov |

(Continued)

OTHER PUBLICATIONS

Maynard et al "Multiwavelength ellipsometry for real-time process control of the plasma etching of patterned samples" J.Vac. Sci. Technol. B XP-000729002. 15:1: 109-115 (Jan./Feb. 1997).

*Primary Examiner* — Jamil Ahmed
(74) *Attorney, Agent, or Firm* — Browdy and Neimark, P.L.L.C.

(57) ABSTRACT

A method and system are presented for use in controlling a process applied to a patterned structure having regions of different layered stacks. The method comprises: sequentially receiving measured data indicative of optical response of the structure being processed during a predetermined processing time, and generating a corresponding sequence of data pieces measured over time; and analyzing and processing the sequence of the data pieces and determining at least one main parameter of the structure. The analyzing and processing comprises: processing a part of said sequence of the data pieces and obtaining data indicative of one or more parameters of the structure; utilizing said data indicative of said one or more parameters of the structure and optimizing model data describing a relation between an optical response of the structure and one or more parameters of the structure; utilizing the optimized model data for processing at least a part of the sequence of the measured data pieces, and determining at least one parameters of the structure characterizing said process applied to the structure, and generating data indicative thereof.

24 Claims, 2 Drawing Sheets

Related U.S. Application Data (60) Provisional application No. 61/683,215, filed on Aug. 15, 2012.

(51) Int. Cl.
*G01N 21/47* (2006.01)
*G01B 11/24* (2006.01)
*G01B 11/06* (2006.01)

(56) References Cited

U.S. PATENT DOCUMENTS

| | | |
|---|---|---|
| 2008/0009081 A1 | 1/2008 | Madriaga et al. |
| 2011/0025839 A1 | 2/2011 | Trupke et al. |
| 2012/0008147 A1* | 1/2012 | Finarov .................. G01B 11/24 356/601 |

* cited by examiner

OPTICAL METROLOGY FOR IN-SITU MEASUREMENTS

TECHNOLOGICAL FIELD

The present invention is generally in the field of optical measurement techniques, and relates to an optical method and system for use in the in-situ measurements of parameters of structures being processed/manufactured. The invention is particularly useful in semiconductor industry for controlling various processes in the manufacture of patterned structures (semiconductor wafers).

BACKGROUND

Generally, in the field of production of patterned structures, it is known to control the process of pattern creation by one or more of integrated, in-situ, and stand alone optical measurement techniques.

For example, U.S. Pat. No. 6,764,379, assigned to the assignee of the present application, describes the use of integrated technique and also a combination of the integrated and in-situ techniques for monitoring the processing of a stream of substantially identical articles progressing on a production line. First, an in-situ technique is applied to identify and terminate the processing upon detecting an end-point signal, where the latter corresponds to a predetermined value of a certain parameter of the article being processed. Upon completing the processing in response to the end-point signal, generated by an end-point detector continuously operating during the processing of the article, integrated monitoring is applied to the processed article to measure the value of said parameter. The measured value of the desired parameter is analyzed to determine a correction value to be used for adjusting the end-point signal to be used for properly terminating the processing of the next article in the stream.

General Description

There is a need in the art for a novel approach for in-situ monitoring a process of manufacturing patterned structures of the type having different layered stacks within a structure.

Generally, advantage of in-situ measurements over integrated and stand alone techniques resides in possibility of measuring on the same structure as the process advances. This enables controlling the product and process parameters in real time, practically without interrupting the process, and enabling real-time detecting the process end-point and controlling the process parameters. The interpretation of in-situ measured data is a complicated task, and conventional techniques of the kind specified are not sufficiently accurate, mainly because in-situ measurements are affected by irregular environment characteristics, mechanical movement of the structure under processing/measurements, etc. Also, in-situ optical measurements unavoidably have lower spatial resolution, as they require relatively large size of a measurement spot. In case of a patterned structure having different layers stacks the use of such a large spot results in that a measurement spot includes portions of different stacks, e.g. different patterns. More specifically, in-situ optical, e.g. spectral, measurements are usually done with spot that is much larger than the specially designed scribe line test structures (50 by 50 micron). Usually, spot size on the wafer surface is about a few millimeters and higher in diameter, that is comparable/larger than the die size. Measured signal in case of such "large" spot could be a combination of signals reflected from all features in the measured spot. In other words, the in-situ optical measurements have strong signal dependency on wafer's pattern.

The present invention provides a novel technique for use in the in-situ optical measurements. This novel technique is based on the inventors' understanding that in-situ optical measurements provide measured data in the form of a sequence of data pieces measured over time as the process applied to the structure proceeds. Such a sequence of data pieces provides a map of structure's profile variation in time. This enables real-time modeling of the structure profile, i.e. optimizing a model describing the relation between the structure profile and optical response of the structure. Thus, the profile parameters of the structure can be extracted from the dynamically optimized model based on the time series of in-situ optical signals (signatures), e.g. spectra, angle-resolved, elipsometric parameters, spectro-ellipsometer (SE) parameter, etc.

It should be understood that real-time profile modeling approach of the invention is different from the regular scatterometry (optical critical-dimension, OCD) modeling, in both the profile definition and algorithms for data interpretation. The real-time profile modeling technique of the invention may utilize standard OCD and/or other measurement results of any relevant feature or features on the same patterned structure (wafer) to fine tune the accuracy and timing of real-time profile predictions, both for the current run (using pre measurements or splitting the real-time dataset series into sub-series which can be analyzed with different algorithms) and for next run (using after-process measurements). It should also be noted that multiple optical detectors (of the same or different types) can be used for in-situ measurements of the same spot on the structure and/or different multiple spots on the structure.

The present invention provides a dedicated technique for enhancing the stability and robustness of measurements utilizing the real-time profile modeling of the invention. According to the invention, a time sequence of several measurements is used in different ways to allow tracking of the processes and to use constraints that connect the sequence in a way that is consistent with the process and modeling.

In some embodiments, the invention utilizes a combined time sequence of measurements. Instead of using looking at each signature (e.g., spectrum) as representing specific structure, as traditionally done in scatterometry measurements, the real-time profile modeling approach of the invention is based on analyzing, at any point of time (in real time during the process), the entire set of measurements, being a sequence of data pieces measured over time from the beginning of the process till the current moment. In other words, the technique of the invention uses the history of the process, where all the already measured frames/signals (preceding measured data pieces) are available for the analysis, and always the entire sequence of the results of interpretations of previously measured spectra is used for trend analysis and prediction. A prediction model is build at each point of time based on the entire sequence of available previous interpretation results, and is used for automatic estimate of starting point for next interpretation(s) and for automatic estimate for interpretation ranges. In addition, a prediction model can trigger switching between different search algorithms in the sequence of time frames, to either allow faster convergence when stable solution is achieved or reduce the number of floating parameters by opening/closing parameters based on prediction.

In some other embodiments, the invention provides measured data processing technique utilizing multiple raw data signals. This technique allows direct fit of time derivative of the process (e.g. etching) related parameters. A software product or user can define variable parameters that can be used for this purpose, e.g. the main etch parameters such as the etch rate in different materials. For these parameters, prior information may be also used as s starting point or prediction (for example averaged, known or expected etch rate). The data analysis technique first tests whether previous fit results define a clean enough prediction trend and/or match an expected trend. If this is the case, then the successive measured spectra are fitted in groups, adding the derivative with time of fit parameter as fit parameters themselves. Actual calculation can be done only for part of the spectra in the group and results are interpolated along time axis the rest of spectra. The time sequence of measured data pieces indicative of optical responses (e.g. spectra) of the structure under measurements is automatically segmented in groups according to estimated linearity of a change of the optical response (spectral change) in time.

In some embodiments, the invention utilizes confidence factor calculation and use. The purpose of this feature is to give some quantitative measure of what is the confidence of interpretation results for some measured data (spectrum) in measurement time sequence. Low confidence of fit results is defined based on the difference between results and trend for the change for fitted parameters values, in time. It is possible to implement this feature in a very basic way, for example calculating the ratio between the deviation of the current point from estimated trend for previous in time points, especially for process substeps where the expected trend/process rate is known. The larger the deviation compared to the standard deviation of the estimated trend, the lower is the confidence limit of the current point. This information may be integrated with the estimation of the trend, to make it more robust to cases where the estimation of the trend becomes unclear. This is in particular relevant when working online where not all signals may be interpreted in time. Confidence factor may be used to filter certain points from the trend estimation or prediction models to make them more robust.

Thus, according to one broad aspect of the invention, there is provided a method for use in controlling a process applied to a patterned structure having regions of different layered stacks. The method comprises:
(a) sequentially receiving measured data indicative of optical response of the structure being processed during a predetermined processing time, and generating a corresponding sequence of data pieces measured over time;
(b) analyzing and processing the sequence of the data pieces and determining at least one main parameter of the structure, wherein said analyzing and processing comprises:
  i) processing a part of said sequence of the data pieces and obtaining data indicative of one or more parameters of the structure,
  ii) utilizing said data indicative of said one or more parameters of the structure and optimizing model data describing a relation between an optical response of the structure and one or more parameters of the structure;
  iii) utilizing the optimized model data for processing at least a part of the sequence of the measured data pieces, and determining at least one parameters of the structure characterizing said process applied to the structure, and generating data indicative thereof.

In some embodiments, the obtained data indicative of the one or more parameters includes information about one or more secondary parameters of the structure, being relatively weak and slowly varying with the process applied to the structure; and/or one or more secondary parameters of the structure, being substantially not affected by the process applied to the structure. The at least one determined parameter of the structure characterizing said process applied to the structure typically includes at least one structure parameter being relatively strong and fast varying with the process applied to the structure.

Secondary parameters are parameters that either are substantially not affectable by the process applied to the structure or are relatively weak and slowly varying with the process, while main parameters are relatively strongly and quickly varying with the process.

The part of the sequence of data pieces from which said one or more parameters is obtained comprises preceding data pieces corresponding to an initial time interval of the processing time. The at least part of the sequence processed for the determination of the at least one parameter of the structure characterizing the process applied to the structure comprises the data pieces corresponding to a successive time interval of the processing time.

In some embodiments, the processing of the preceding data pieces comprises: utilizing data about behavior of said one or more parameters of the structure during application of said process, and obtaining data about each of said one or more parameters at one or more points of time within the initial time interval corresponding to the one or more of the preceding data pieces; and generating model optimization data. The model optimization data may comprise a fixed value for each of the one or more parameters, or a fixed range of change of value for each of the one or more secondary parameters over time.

The at least one parameter characterizing the process applied to the structure may comprise at least one of the following: an etch depth, thickness of a material being deposited, and thickness of a remaining material during a material removal process. The one or more parameters for which data is obtained while processing initial data pieces may comprises at least one of side wall angle, rounding, thickness of at least one layer in the stack (e.g. underneath layer).

In some embodiments, the determination of the at least one parameter of the structure characterizing the process applied to the structure comprises segmenting in groups the at least a part of the sequence of the measured data pieces, according to estimated linearity of time change of the optical response.

According to another broad aspect of the invention, there is provided a control system for use in controlling a process applied to patterned structures. The control system is a computer system comprising:
data input utility for receiving measured data indicative of optical response of a structure being processed by said process during a predetermined processing time, and generating a corresponding sequence of data pieces measured over time;
a processing utility configured and operable for analyzing and processing the sequence of the data pieces and determining at least one main parameter of the structure characterizing the process applied to the structure, wherein said processing utility comprises:

a structure analyzer configured and operable for processing a part of said sequence of the data pieces and obtaining data indicative of one or more parameters of the structure, a model optimization module configured and operable for utilizing said data indicative of the one or more parameters of the structure and generating model optimizing data for optimizing a model describing a relation between an optical response of the structure and parameters of the structure;

a model-base parameter calculator configured and operable for utilizing the optimized model data for processing at least a part of the sequence of the measured data pieces, and determining the at least one parameter of the structure characterizing said process applied to the structure, and generating data indicative thereof.

In yet further aspect of the invention, it provides a measurements system for in-situ monitoring a process applied to a patterned structure having regions of different layered stacks, wherein the measurement system comprises an optical measurement unit configured and operable for performing optical measurements on a structure being processed during a certain processing time t, and the above-described control system for receiving the measure data, generating the corresponding sequence of data pieces measured over time, and processing said sequence and determining the at least one parameter of the structure characterizing the process being applied to the structure. The optical measurement unit comprises an illumination assembly for illuminating a measurement spot on the structure being processed to cause an optical response of the structure, and a detection assembly for detecting the optical response over said processing time t and generating measured data corresponding to the detected optical response over time.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

The present invention provides a novel method and system for use in process control in the manufacture of a patterned structure of a type having regions of different layered stacks, such as semiconductor wafers.

Figure 1:
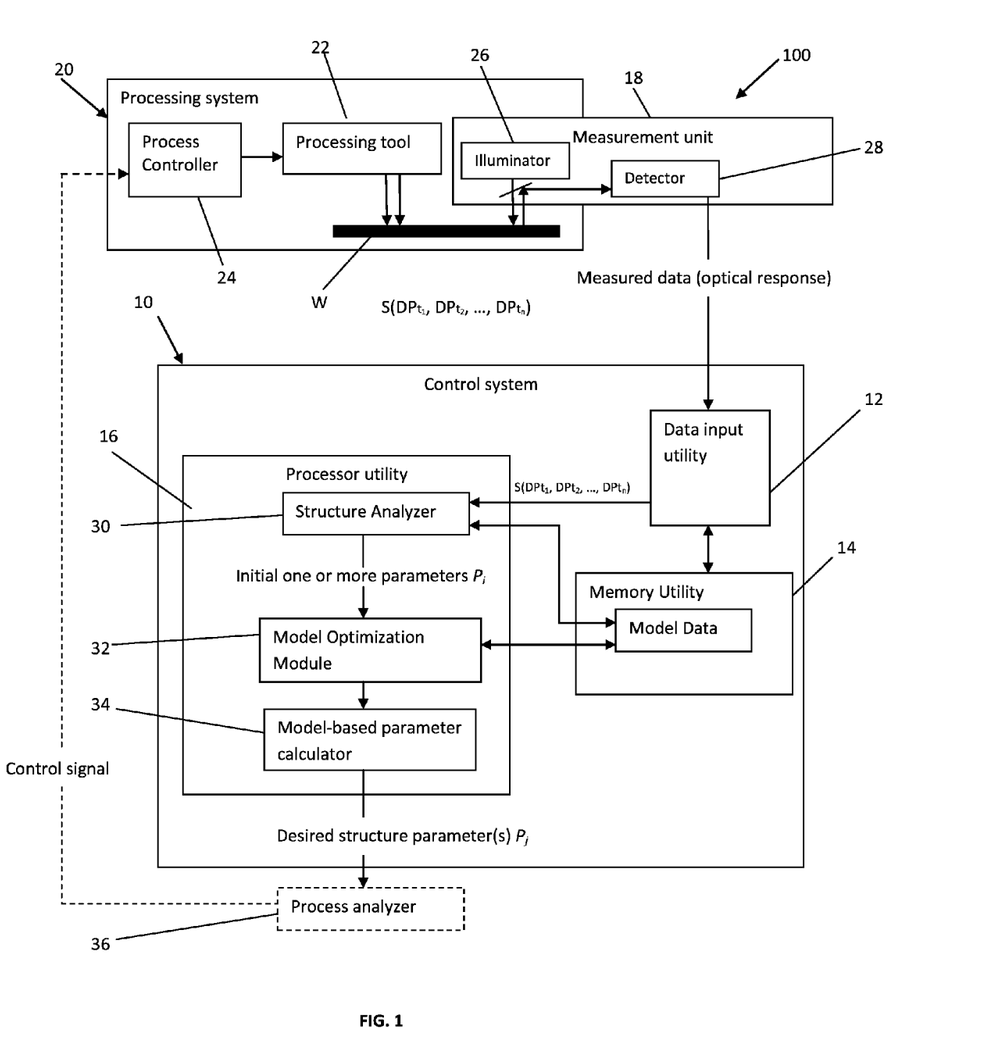
FIG. 1 illustrates a block diagram of the main functional elements of a system of the present invention for or use in controlling a manufacturing process of patterned structures.

Referring to FIG. 1, there is illustrated, by way of a block diagram, a control system, generally designated 10, configured and operable according to the present invention for processing optical measured data obtained from a patterned structure under processing, such as etching or polishing. The control system 10 is typically a computer system having inter alia such modules/utilities (software and/or hardware) as data input utility 12, memory utility 14, and data processing and analyzing utility 16.

As shown in the figure, the control system 10 is a part of a measurement system 100 and is associated (connectable, via wires or wireless signal transmission, to) an optical measurement unit 18 and possibly also a processing system 20. The construction and operation of such measurement unit and processing system are know per se and do not form part of the present invention, and therefore need not be specifically described, except to note the following: A structure W undergoes certain processing, such as etching, by a processing tool 22, whose operation is controlled by a process controller 24. The measurement unit 18 is configured and operable for performing in-situ optical measurements on a patterned structure such as a semiconductor wafer W progressing on a production line. To this end, the measurement unit 18 includes appropriate illumination and detection assemblies 26 and 28. These assemblies may have any suitable configuration, operable in dark and/or bright field detection mode. The optical measurement unit 18 applies optical measurements, e.g. spectrometric measurements, to the structure W being processed during a certain processing time t.

It should be noted, although not specifically shown, that the measurement unit 18 may be configured for additionally carrying out integrated measurements, which can be carried using the same or different illumination and/or detection assemblies. The principles of the integration measurements are known per se and need not be described in details.

For the purposes of the present invention, the integration measurements might be additionally used to provide data about one or more parameters of the structure. These may be for example structure parameters substantially unaffectable by the process.

As will be described more specifically further below, in some embodiments of the invention, secondary parameter(s) may be determined at the initial stage of measured data processing and then used for determining one or more desired parameter(s) of the structure characterizing the process parameter(s) that is/are to be controlled. Such structure parameter(s) is/are referred thereto as main parameter(s), being relatively strong and quickly varying with the process applied to the structure. In some embodiments, the determination of one or more secondary parameters may utilize one or more parameters measured by the integration measurement system. It should also be noted, although not specifically shown that the detection assembly of the in-situ measurement unit, as well as the integrated measurement unit, if any, may utilize multiple (at least two) detectors of different types.

For example, for basic lithography processes, the one or more main, process-related, structure parameters (usually one or very few) include etch depth, thickness of a layer being deposited, thickness of a remaining layer in the material removal process, etc., that actually describe the in-situ process. As for the secondary process-related structure parameters, they may for example include side wall angle, rounding, etc., that are relatively weak and are slowly varying with the process, or practically having substantially "constant" profile, i.e. parameters that do not vary with the process or vary within a certain well defined range, such as thicknesses of some layers (typically an underneath layer) that can vary from structure to structure but are the same for each structure (determined only by previous process steps).

Turning back to FIG. 1, output of the detector 28 (e.g. appropriately formatted for transmission to the control system 10) is thus in the form of a sequence, $S(DP_{t_1}, DP_{t_2}, \ldots, DP_{t_n})$, of data pieces DP corresponding to sequential measurement sessions performed at successive points/segments $t_1, t_2, \ldots, t_n$ of at least a part of the processing time t. Each such measured data piece is indicative of an optical response of the structure within the illuminated spot thereon (measurement spot) at a respective time point/segment of the processing time.

The control system 10 may, in some embodiments, utilize certain process-related data and/or structure-related data, which may be a-priori known and/or obtained during the initial measurement session(s), and these data may be stored in the memory utility 14. Also stored in the memory 14 is certain model data, including one or more models. The model describes a relation between the optical response of the structure and one or more parameters of the structure. The model data is used for interpreting the measured data to enable determination of various structure parameters. A change/profile of one or more structure parameters during at least a part of the processing time is indicative of one or more process parameters that is/are to be controlled.

Thus, measured data corresponding to successive measurements over time is sequentially received by the input utility 12 of the control system 10, which generates in a corresponding sequence of data pieces, $S(DP_{t_1}, DP_{t_2}, \ldots, DP_{t_n})$, which is processed by the processing utility 16. The processing utility 16 includes a structure analyzer module which is configured and operable for analyzing the sequence of measured data pieces, and determining data indicative of one or more parameters, $P_i$, of the structure W. The latter is/are then used by a model optimization module 32 of the processing utility 16 for optimizing the model data. As the processing of the structure and the optical measurements thereon proceed, the model data may be dynamically optimized based on the preceding measured data pieces for interpreting/analyzing the successive measured data pieces. A model-based parameter calculator utility/module 34 utilizes the so-obtained optimized model data for analyzing the successive measured data pieces and determining at least one parameter of the structure characterizing the process applied to the structure, and generating output data indicative of such at least one desired parameter.

The desired structure parameters are those characterizing one or more tunable/controllable parameters of the process applied to the structure and may be used by a process analyzer 36 to generate respective control signal to the processing tool. The process analyzer 36 may be a part of the control system 10, or may be a part of the process controller of the processing system, or a separate computer system interconnectable between the control system 10 and the processing system; as well as software utilities of the process analyzer may be appropriately distributed between the control system and the processing system, as the case may be.

In some embodiments, the initially obtained data about one or more parameters $P_i$ of the structure include preliminary estimate, e.g. range of values, of a specific parameter, which data is used for optimizing the model, and then the successive data pieces are analyzed using the optimized model to determine the exact value $P_j$ of the same parameter.

In some other embodiments, the initial parameters $P_i$ are secondary parameters which are either constant parameters of the structure or parameters less sensitive to the process applied to the structure, as compared to the main structure-related parameters $P_j$ that are used to characterize the process. It should be understood that the main parameters $P_j$ may include the values of one or more of the secondary parameters $P_i$ as well.

Figure 2:
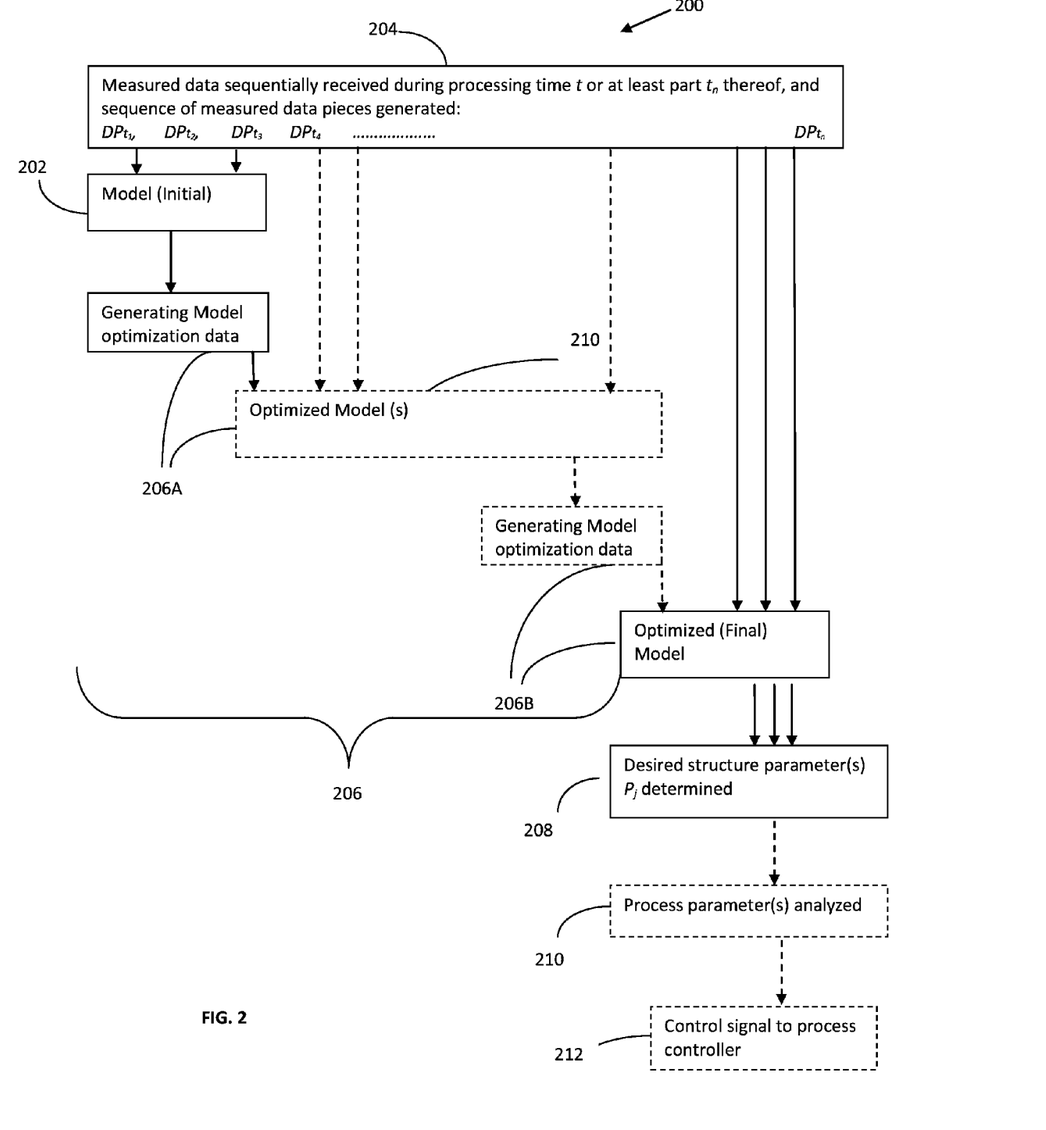
FIG. 2 is a flow chart of an example of a method of the present invention for processing in-situ measured data during a process applied to a patterned structure.

Reference is made to FIG. 2 exemplifying a flow chart 200 of a method of the present invention for use in monitoring a process applied to a patterned structure of the kind having regions of different layered stacks. First, initial model data is provided (step 202) and stored in a memory utility accessible by the control system (e.g. the memory utility is a part of the control system, or of a separate storage device accessible via a communication network). As indicated above, the model data describes a relation (function) between the optical response of the structure (corresponding to the type of optical measurements used) and the parameters of the structure, including those characterizing the process being applied to the structure.

Measurements are continuously or periodically applied to the structure while the structure is being processed, during a processing time t. The measured data is sequentially received at the control system during at least a part $t_n$ of the processing time t and the control system operates to dynamically generate a sequence, $S(DP_{t_1}, DP_{t_2}, \ldots, DP_{t_n})$ of measured data pieces (step 204). Generally, a part (initial part) of the sequence of the measured data pieces is analyzed using the initial model data, model optimizing data is determined, and the optimized model is generated (step 206). The optimized model is then used for the analysis of the successive data pieces and at least one desired parameter of the structure is determined (step 208). As indicated above, the model optimization may include "quick" determination (i.e. from one or a few initial data pieces) of one or more parameters of the structure the values of which can be fixed in the model.

As shown in this specific but not limiting example, the model data optimization stage 206 may also be a dynamic procedure, namely each (or periodically taken) set/stream of the preceding data pieces is used for determining one or more parameters for optimizing the model data (steps 206A), the so-optimized model data is used for determining one or more parameters of the structure from a successive set/stream of data pieces and these parameters enables further optimization of the model data (steps 206B), and so on, as shown in the figure in dashed lines. Such dynamic optimization of the model data proceeds until the final optimized model data is obtained allowing determination of the at least one desired parameter of the structure with sufficient accuracy.

More specifically, the analysis of the initial/preceding part $S_k$ of the sequence of the data pieces, corresponding to an initial/preceding time interval $t_k < t_n$, is used to obtain initial/preceding data about one or more parameters (e.g. determine one or more secondary parameters) of the structure, as will be described further below. Such initial/preceding data about one or more parameters (e.g. values or range of values of secondary parameters) is used for optimizing the model data (steps 206A, 206B). For example, the values or ranges of values of secondary parameters are "fixed" in the model.

The measured data pieces continue to be received at the control system during successive measurement sessions, and analyzed by the control system using the optimized model data, to thereby determine value(s) of structure parameter(s) $P_j$ (e.g. main parameters) characterizing the processing of the structure (step 208). As described above, the part of the structure parameters characterizing the processing, e.g. at least one such parameter, may be further used for dynamically optimizing the model, and the optimized model is then used for the determination of other parameters of the structure or determination of the value of the same parameter with higher accuracy. The determined structure parameters may be used for estimating/analyzing one or more of the process parameters that affect such main structure parameters (optional step 210) and corresponding control signals are generated to the processing system.

There are several options for analysis of the initial sequence of data pieces and the use of the results for model data optimization and estimation/determination of the at least one parameter of the structure characterizing the structure. The use of such parameter attributes as a secondary and main parameters (or initially and successively determined parameters) during the fitting of the process sequence together with working with entire set of measurements performed from the beginning of the process till the current moment allow performance optimization.

For all "constant" secondary parameters, the processing utility uses as many points as required to find out a proper value and fix this value as early in the measurement sequence as possible. For all "non-constant but weakly variable" secondary parameters, the processing algorithm may assume small consistent changes through a process, or maybe even assumed constant for a localized (in time) process sequence steps. For the main parameters, the processing algorithm may assume expected behavior with time based on "known" average process rate (e.g. etch rate, or material removal rate, or material deposition rate), and can assume similar behavior for a localized (in time) process sequence steps (locally linear or non liner dependence with the same function).

Similar definition of profile parameters is done for all patterns (stacks) used for calculation of the expected returned signal (optical response). Parameters of different stacks are connected in a flexible process related way. Calculation of the optical responses or signatures (spectra) from multiple stacks could be used for accounting for the relative weights of the stacks and fine geometrical definitions of the placement of stacks in the measurement spot. In addition, characteristics of incident light (optical system) is taken into account in calculations.

The measurement unit may utilize standard OCD and/or other measurement results (including same/different in-situ detectors).

In some embodiments, the control system of the invention utilizes external injection of preliminary measurements for determination of one or more parameters of the structure. For example, as indicated above, the secondary "constant" parameters that do not vary with the process need to have their value determined and fixed as soon as possible (either before the process starts or during the first, initial part of the process). To this end, as indicated above, preliminary measurement could be done in the same or other process chamber by another in-situ sensor, and/or outside the process chamber using integrated metrology and/or any stand alone tool, to determine relevant structure and/or process parameters (all or at least some profile parameters, including thicknesses of deposited layers) for in-situ measurements. These values could be injected into the model ("constant" profile parameters) and/or used as a starting point for interpretation (main and secondary process parameters). Measurements can be done on all relevant sites on the wafer, and only relevant information will be injected. The example of a combined system comprising In-Situ (End-Point) and Integrated Metrology sub-systems useful for the present invention technique (e.g. based on zero-order normal incidence spectrophotometer) is disclosed in U.S. Pat. No. 6,764,379 assigned to the assignee of the present application. This document is therefore incorporated herein by reference with respect to these specific examples.

In some embodiments, the control system of the invention utilizes external injection preliminary measurements for spectral information. More specifically, signals returned (e.g. reflections) from different stacks within the measurement spot are combined into the in-situ common signature (e.g. reflectance spectra). Each one of these different stacks can be measured by integrated and/or stand alone system (e.g. commercially available from Nova Measuring Instruments Ltd.) providing measurement of the relatively small spot of 10-50 microns at exact location on the wafer. These precise preliminary measurements may be injected and used to "modify" the measured in-situ signal, by removing from this signal reflection coming from non periodical structures/patterns in the wafer that are hard to model. Such removal of influence of non periodical patterns allows for better converging the processing of measurement of endpoint for memory in-die array.

In some embodiments, the control system of the invention utilizes external injection of post-measurements for profile parameters. More specifically, in addition to preliminary measurements information, post measurement data can also be used, if needed, to adjust certain parameters of the solution or recalculate certain default factors and assumptions used by the data processing algorithm. These values may be injected into the model ("constant" profile parameters) and/or used as a starting point for interpretation.

In some embodiment, internal injection for profile parameters can be used. In majority of modern processes there are multiple steps used to generate the required result in the same chamber. In-situ monitoring of the entire process may cover all the steps, or any subset of steps. There may be a case where instead of single recipe for all steps multiple recipes are used, each recipe being optimized for a certain process step. In this case, each previous recipe in the sequence may inject all relevant parameters to the next recipe. These values are injected into the model ("constant" profile parameters) and/or used as a starting point for interpretation (main and secondary process parameters).

As indicated above, the measurement unit may utilize multiple illumination/detection units or multiple detectors associated with the same illumination assembly, thus allowing parallel (simultaneous) processing of information from multiple detectors. In case additional detectors are used in-situ, information from these detectors can be used in real time to improve prediction results, both as injection of relevant information about the process, and as an additional signal/s that can be used together to do the job. If multiple detectors are "looking" at different locations on the wafer, then across the wafer signatures (optical responses) may be determined and controlled through the process. This is especially important for the processes where wafer position changes relative to the detector/s during the process. One of the examples of such processes is Chemical Mechanical Planarization (CMP), where wafers are moving above the fixed detectors. Information about relative position of the wafer to the detectors together with the simultaneous interpretation of the information from multiple detectors allows to control both the CMP rate and the across the wafer uniformity.

Information from different detectors and/or process related parameters, such as plasma/gas/composition/etc. changes may be incorporated into the data processing algorithm to allow optimal convergence. A particular example is the impact of change in effective ambient (whether it is plasma gas or etch by product) on the measured spectrum, where for some process steps the effective ambient of the measurement cannot be approximated to vacuum without affecting the accuracy of the reported geometrical profile parameters. In such cases, the ambient needs to be accurately described (optically). Such ambient might depend on tool/process/wafer stack/gas/plasma/etc. parameters, and receiving such detailed instantaneous information from the process tool can help to select the right ambient model for the instantaneous model representation and accurate profile measurement.

The invention claimed is:

1. A method for use in controlling a multi-step process of manufacturing patterned structure having regions of different layered stacks, the method comprising performing in-situ optical measurements of a structure while said structure sequentially undergoes at least a subset of the multiple steps of said process, said performing of the optical measurements comprising:
   (a) sequentially receiving measured data over a processing time as the process applied to the structure proceeds through said at least subset of the multiple steps, the measured data being indicative of optical response of the structure formed by multiple signals from the different layered stacks in the structure being processed during said predetermined processing time, and being indicative of a map of variation of structure's profile during the processing corresponding to behavior of one or more parameters of the structure during one or more steps of the process; and
   (b) analyzing and processing the measured data to determine one or more parameters of the structure, said analyzing and processing comprising utilizing said map of the structure's profile variations and performing fitting procedures and extracting said one or more parameters of the structure wherein said utilizing of the map of the structure's profile variations and performing fitting procedures comprises dynamically optimizing a model, which describes a relation between the structure profile and an optical response of different patterns from different layered stacks in a structure similar to the structure under measurements; and performing the fitting using the dynamically optimized model.

2. The method according to claim 1, wherein said analyzing and processing comprises: analyzing the sequentially received measured data and generating a corresponding sequence of measured data pieces measured over said processing time.

3. The method according to claim 2, wherein said analyzing and processing comprises: analyzing, at any point of time within said processing time, a set of measurements, being a sequence of the measured data pieces measured over time from the beginning of said processing time till said point of time.

4. The method according to claim 1, wherein said utilizing of map of the structure's profile variations corresponding to behavior of one or more parameters of the structure during one or more steps of the process comprises defining secondary and main parameters to be, respectively, previously and successively determined in the fitting procedure, such that the previously determined secondary parameters are used for optimizing the model for successive determination of the main parameters of the structure.

5. The method according to claim 1, comprising at least one of the following: (1) using multiple recipes, each recipe being optimized for at least one process step in said at least subset of steps; and (2) using a single recipe for at least some steps in said at least subset of the multiple steps.

6. The method according to claim 1, wherein said dynamically optimizing of the model comprises internal injection of values of the structure's profile parameters, such that preceding recipe in the sequence injects one or more parameters' values to the successive recipe in the sequence.

7. The method according to claim 6, characterized by one of the following: (i) the one or more values are injected into the model to form constant profile parameters; and (ii) the one or more values are injected into the model to form a starting point for interpretation of the measured data.

8. The method according to claim 6, wherein the one or more values are injected into the model to form a starting point for interpretation of the measured data, said analyzing of the measured data comprises, at each point of time building a prediction model based on the entire sequence of the measured data pieces measured over time from the beginning of said processing time till said point of time and corresponding entire sequence of model-based interpretation results including said values of the parameters; and using the prediction model for automatic estimate of the starting point for next interpretation of the measured data piece and for automatic estimate for interpretation ranges.

9. The method according to claim 6, wherein said dynamically optimizing the model further comprises external injection of one or more values of the structure's profile parameters determined in post measurements.

10. The method according to claim 9, wherein said one or more values externally injected are used to adjust one or more model parameters or recalculate certain default factors and assumptions of the data processing and analyzing.

11. The method according to claim 9, characterized by one of the following: using said one or more values externally injected to form constant profile parameters; injecting said one or more values into the model to form a starting point for interpretation of the measured data.

12. The method according to claim 4, wherein the secondary parameters comprises at least one of the following types of parameters: one or more parameters which relatively weak and slowly varying with the process applied to the structure; one or more parameters which are substantially not affected by the process applied to the structure.

13. The method according to claim 4, wherein optimizing of the model based on the secondary determined parameters comprises: for all constant values of the secondary parameters, finding out an optimal value and fixing this value in the measurement sequence; and for all non-constant but weakly variable secondary parameters, defining a range of consistent changes through the process and/or defining as constant for a localized process sequence steps.

14. The method according to claim 13, further comprising: for the main parameters, defining expected behavior with time based on known average process rate.

15. The method according to claim 14, wherein the process rate comprises one or more of the following: etch rate, material removal rate, material deposition rate.

16. The method according to claim 14, further comprising: for the main parameters, defining similar behavior for a localized process sequence steps.

17. The method according to claim 1, wherein said one or more parameters of the structure characterizing the process applied to the structure comprise at least one of an etch depth, thickness of a material being deposited, and thickness of a remaining material during a material removal process.

18. The method according to claim 4, wherein said one or more secondary parameters comprises one or more of the following: side wall angle, rounding, thickness of at least one layer in the stack.

19. The method according to claim 1, comprising segmenting in groups said measured data of the at least subset of steps according to estimated linearity of time change of the optical response of the structure.

20. The method according to claim 1, wherein said measured data comprises spectral data.

21. The method according to claim 1, wherein said structure sequentially undergoes said at least subset of the multiple steps of said process in the same processing chamber.

22. A control system for use in controlling a multi-step process of manufacturing of patterned structures, the control system being a computer system configured and operable for performing the method of claim 1.

23. A control system for use in controlling a multi-step process of manufacturing of patterned structures, the control system being a computer system and comprising:
   (a) data input utility to receive measured data indicative of in-situ measured optical response of a structure being processed by at least a subset of the multiple steps of said process during a predetermined processing time, and generating a corresponding sequence of data pieces measured over said time; and
   (b) a processing utility operable to analyze and processing the sequence of the data pieces and determining at least one parameter of the structure characterizing the process applied to the structure, wherein said processing utility comprises:
      i) a structure analyzer operable to analyze, at any point of time within said processing time, a set of measurements, being a sequence of the measured data pieces measured over time from the beginning of said processing time till said point of time, and being indicative of a map of variation of structure's profile during the processing corresponding to behavior of one or more parameters of the structure during one or more steps of the process,
      ii) a model optimization module operable to utilize said map of the structure's profile variations and dynamically optimizing a model, which describes a relation between the structure profile and an optical response of different patterns from different layered stacks in a structure similar to the structure under measurements;
      iii) a model-based parameter calculator operable to utilize the dynamically optimized model and performing fitting procedures and extracting said one or more parameters of the structure from the dynamically optimized model, and generating data indicative thereof.

24. A measurements system for in-situ monitoring a process applied to a patterned structure having regions of different layered stacks, the measurement system comprising:
   an optical measurement unit operable to perform an optical measurements on a structure being processed during a certain processing time t, the optical measurement unit comprising an illumination assembly for illuminating a measurement spot on the structure being processed to cause an optical response of the structure, and a detection assembly for detecting the optical response over said processing time t and generating measured data corresponding to the detected optical response over time, and
   the control system of claim 23 to receive the measure data, generate the corresponding sequence of data pieces measured over time, and process said sequence and determine the at least one parameter of the structure characterizing the process being applied to the structure.

* * * * *